(12) United States Patent
Maeda et al.

(10) Patent No.: US 7,585,628 B2
(45) Date of Patent: Sep. 8, 2009

(54) METHOD AND APPARATUS FOR ANALYZING NUCLEIC ACID AMPLIFICATION

(75) Inventors: Koshi Maeda, Hitachinaka (JP); Shinichi Fukuzono, Hitachinaka (JP); Kokichi Sugano, Urayasu (JP)

(73) Assignees: Hitachi High-Technologies Corporation, Tokyo (JP); Tochigi Prefectural Office, Utsunomiya-shi, Tochigi (JP)

( * ) Notice: Subject to any disclaimer, the term of this patent is extended or adjusted under 35 U.S.C. 154(b) by 207 days.

(21) Appl. No.: 11/227,233

(22) Filed: Sep. 16, 2005

(65) Prior Publication Data

US 2006/0073503 A1  Apr. 6, 2006

(30) Foreign Application Priority Data

Sep. 27, 2004  (JP) .............................. 2004-279214

(51) Int. Cl.
*C12Q 1/68* (2006.01)
(52) U.S. Cl. .......................................... 435/6; 435/91.2
(58) Field of Classification Search ........................ None
See application file for complete search history.

(56) References Cited

U.S. PATENT DOCUMENTS 5,759,821 A  6/1998  Teasdale

FOREIGN PATENT DOCUMENTS

EP          1 288 314 A2    3/2003
WO     WO 2004/007755 A2   1/2004

OTHER PUBLICATIONS

Jobst Landgrebe et al., "Efficient Design and Analysis of Two Colour Factorial Microarray Experiments," Computational Statistics & Data Analysis, vol. 50, No. 2, Sep. 25, 2004, pp. 499-517.
Monica Campagnoli et al., "Analbuminemia in a Swiss Family is Caused by a C→T Transition at Nucleotide 4446 of the Albumin Gene," Clinical Biochemistry, vol. 38, No. 9, Sep. 2005, pp. 819-823.

*Primary Examiner*—James Martinell
(74) *Attorney, Agent, or Firm*—Dickstein Shapiro LLP

(57) ABSTRACT

There is provided a method of detecting or analyzing nucleic acid with a high reliability and reproducibility, capable of sampling target nucleic acid from initial target nucleic acid having not less than two types of sequences different from each other in a ratio which is proportional to that of initial target nucleic acid. A method of detecting or analyzing nucleic acid by sampling target nucleic acid from not less than two types of target nucleic acid samples having base sequences different in at least one base, and subjecting the sampled nucleic acid sample to detection or analysis; comprising steps of: obtaining the number of copies of initial target nucleic acid from the concentration of a nucleic acid in an initial target nucleic acid sample; and sampling the target nucleic acid of a predetermined number or more of copies from the initial target nucleic acid sample.

8 Claims, 6 Drawing Sheets

Method of calculating the number of copies of initial nucleic acid

Adjustment of the number of copies of initial nucleic acid

METHOD AND APPARATUS FOR ANALYZING NUCLEIC ACID AMPLIFICATION

BACKGROUND OF THE INVENTION

1. Field of the Invention

The present invention relates to amplification and detection of a specific sequence contained in target nucleic acid, DNA, detection of polymorphism in a gene, analysis of single nucleotide polymorphism, etc.

2. Background Art

As a method for analyzing polymorphism in a gene, there are the Invader method (Lyamichev, et al., Science 260, 778-783 (1993)) and a single strand conformation polymorphism analysis (SSCP analysis).

In the Invader method, nucleic acid fragments having base sequences specific to two different allelic genes are labeled with different types of fluorescent substances. The nucleic acid fragments, when they completely agree with the target allelic genes, can be detected by detecting the fluorescent substance. Non-patent Document 1 has succeeded in miniaturizing a reaction chamber for the Invader method and reducing the amount of genomic DNA used in the reaction to 0.2 ng (about 40 copies).

In the SSCP method, a two-stranded nucleic acid fragment is amplified, split into single strands, denatured and then subjected to electrophoresis. In this manner, the difference of a single base can be distinguished as a conformational difference and thus analyzed. Furthermore, in the SSCP method, chromosomal deletion, in other words, loss of heterozygosity (LOH) can be detected by determining a quantitative ratio of two different allelic genes containing polymorphism loci, comparing a test sample with a standard sample for the quantitative ratio of the two different allelic genes.

Furthermore, a minute amount of tumor cells is sampled by the single cell sampling system (CLONIS/OL; manufactured by Olympus Corporation) or Laser Capture Microdissection (LCM) Systems (manufactured by BM Equipment Co., Ltd.) and a minute amount of a gene (nucleic acid) is extracted from the tumor cells, amplified and analyzed.

In the prior Art of Non-patent Document 2, it is shown that in sampling nucleic acid for analyzing a microsatellite polymorphism of an allelic gene, the lower the number of copies of the nucleic acid in an aliquot, the larger the degree of variation (dispersion) from a statistical point of view, with the result that the reproducibility of an analysis for detecting an increase or decrease of a chromosome is not high. To overcome this problem, time-release PCR has been proposed in the prior art. In the time-release PCR, a nucleic acid, even if it is present in a low number of copies, can be amplified. Therefore, analysis can be directly performed without performing a step of sampling or dispensing a minute amount of nucleic acid.

[Non-patent Document 1] Abstract of the 26th annual meeting of the Japanese Biology Society of Japan, p778, 2PC-104;

[Non-patent Document 2] Slebos et al., Laboratory Investigation (2004) 84, 649-657.

SUMMARY OF THE INVENTION

Indeed, if the conventional technique shown in Non-patent document 2 is employed, it is possible to suppress the cause of decreasing reproducibility due to sampling and dispensing. However, this method has problems: since sampling and dispensing cannot be made in this method, it is difficult to analyze a plurality of genes taken from the same specimen and reproducible analysis using the same specimen cannot be made. The present inventors experimentally and statistically revealed that such a decrease in reproducibility due to sampling and dispensing might take place not only in analysis for microsatellite polymorphism or single nucleotide polymorphisms (SNPs) but also various analyses requiring sampling and dispensing of a solution containing two different types of nucleic acids. Therefore, an object of the present invention is to provide a method of detecting or analyzing a plurality of different nucleic acids with a high reliability and reproducibility, and a computer program and apparatus useful for such a method.

The present inventors have extensively studied with a view to solve the aforementioned problems. As a result, they statistically proved that analysis could be attained with a requisite accuracy by setting the number of copies of a target nucleic acid sampled from an initial target nucleic acid sample at not less than the number statistically determined. Based on the finding, the present invention was attained. More specifically, a basic constitution of the present invention resides in a method of detecting or analyzing nucleic acid by sampling a pair of target nucleic acid from not less than two types of target nucleic acid samples having base sequences different in at least one base, and subjecting the target nucleic acid sample sampled to detection or analysis; comprising steps of:

obtaining the number of copies of initial target nucleic acid from the concentration of a nucleic acid in an initial target nucleic acid sample; and sampling the target nucleic acid of a predetermined number or more of copies from the initial target nucleic acid sample.

The present invention further provides a method of detecting or analyzing nucleic acid comprising a step of diluting the initial target nucleic acid sample when the number of copies of target nucleic acid to be sampled from the initial target nucleic acid sample exceeds a predetermined value or concentrating the initial target nucleic acid sample when the number of copies of target nucleic acid is lower than the predetermined value. Furthermore, the method of detecting or analyzing nucleic acid may comprise a step of determining whether a nucleic acid sample, in which the number of target nucleic acid to be sampled cannot be adjusted within a predetermined range, is used in a next step or not; and a step of determining, when the nucleic acid sample is used, whether the results are not used or used with a warning described for or a sign attached to the results.

After the step of sampling the target nucleic acid, a step of performing an amplification reaction of nucleic acid or an analysis reaction of nucleic acid is provided as a next step. The present invention is particularly effective in the case where the initial target nucleic acid sample contains genomic DNA such as human genome or plant genome.

In the present invention, it is particularly preferable that the number of copies of the target nucleic acid to be sampled is determined based on the number of copies of the initial target nucleic acid in accordance with a statistic approach using the binomial distribution. However, when the binomial distribution is used, sometimes a complicated and extravagant preparation and calculation are required. For this reason, practically, the number of copies of target nucleic acid is preferably determined by use of an approximation statistic formula of the binomial distribution. The statistic formula will be explained later.

The present invention provides a method of detecting or analyzing nucleic acid by simultaneously amplifying not less than two types of target nucleic acid samples having base sequences different in at least one base by using not less than two types of primers specific to sites of base sequences different in at least one base or not less than two types of primers specific to mutually different base sequences and analyzing a proportion of an amplified amount of nucleic acid of a target gene site in a target nucleic acid; the method comprising steps of:

(a) amplifying nucleic acid by use of an amplification reaction solution containing the target nucleic acid;

(b) estimating the number of copies of the target nucleic acid contained in the amplification reaction solution and the number of copies of initial target nucleic acid based on the amplified amount of nucleic acid after amplification or during amplification;

(c) determining the number of copies of the target nucleic acid required in the amplification reaction solution based on the number of copies of the initial target nucleic acid estimated in accordance with a statistic approach using binomial distribution or an approximation statistic formula of the binomial distribution; and (d) comparing the determined requisite number of copies with the estimated number of copies of the target nucleic acid in the amplification reaction solution.

The method mentioned above may comprise a step of analyzing the proportion of amplified nucleic acid amount of a target gene site in the target nucleic acid, comparing the proportion of a target nucleic acid analyzed as a standard sample with a target nucleic acid analyzed as a test sample; and determining whether a change of a peak ratio differs or not, based on a predetermined threshold. In this method, the number of copies of target nucleic acid in an amplification reaction solution may be determined from the number of copies of initial target nucleic acid in accordance with a statistic approach using the Poisson distribution.

In the method mentioned above a single strand conformation polymorphism analysis (SSCP method) may be used. Furthermore, a nucleic acid microarray using two kinds of fluorescent dye may be used for labeling not less than two types of target nucleic acids with two different fluorescent dyes, respectively, and analyzing the difference in amplification amount of the target nucleic acids based on the difference in fluorescent amount.

By virtue of the methods mentioned above, target nucleic acid can be sampled from the initial target nucleic acid sample containing two types of sequences different to each other in a ratio proportional to that of initial target nucleic acid. The number of copies of the target nucleic acid to be used in analysis for detecting a very small amount of nucleic acid in the initial target nucleic acid sample can be determined. Furthermore, by obtaining a statistical confidence interval with respect to the analyzed results, the analyzed results can be evaluated with a higher accuracy.

DETAILED DESCRIPTION OF THE PREFERRED EMBODIMENTS

The present invention will be explained with respect to novel features and effects partly mentioned above with reference to the accompanying drawings.

Figure 1:
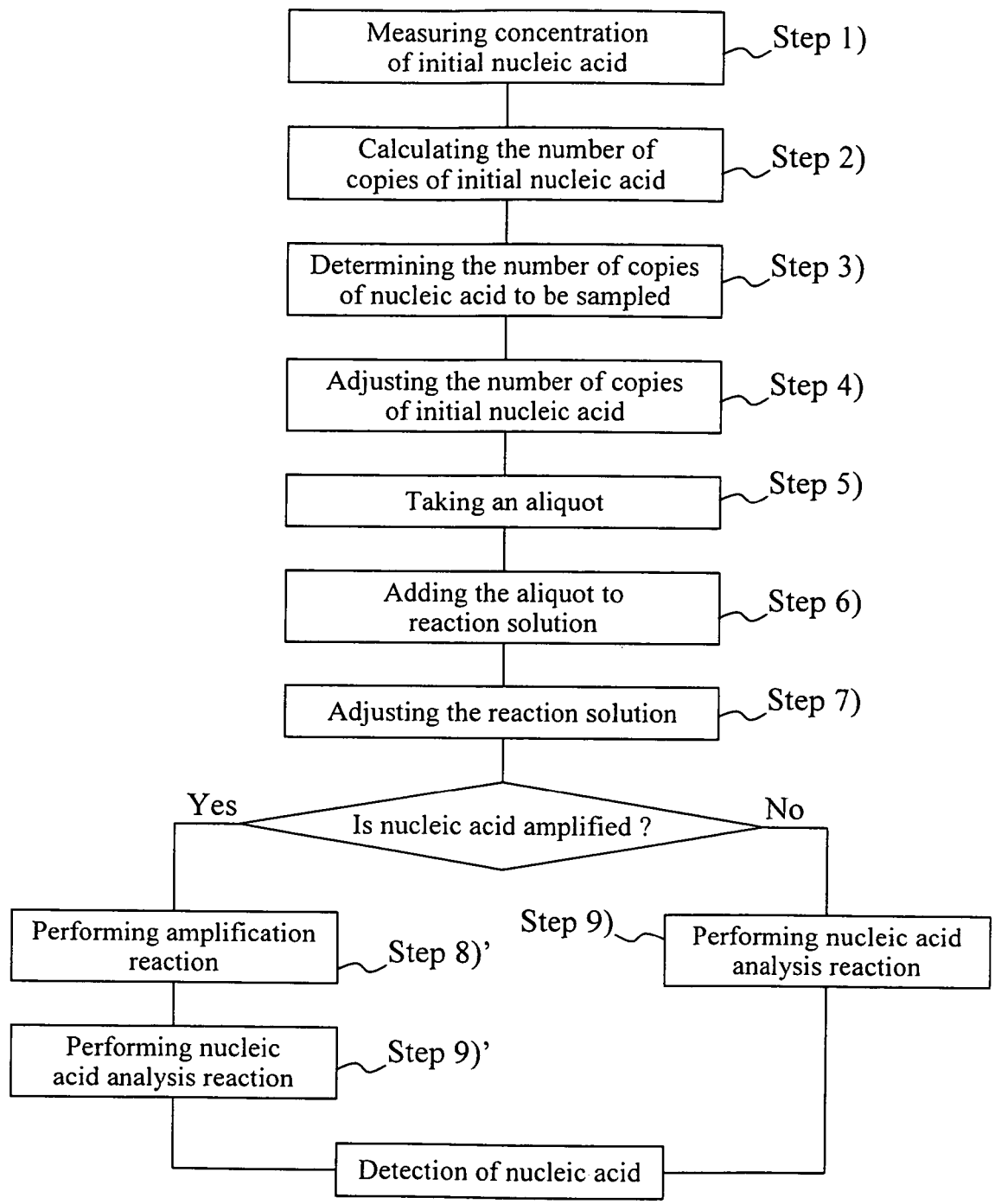
FIG. 1 is a flowchart showing a gist portion of a method of detecting or analyzing nucleic acid according to the present invention.

First, the present invention will be schematically explained. FIG. 1 is a flowchart showing a typical embodiment of the present invention. As is shown in the flowchart of FIG. 1, the concentration of nucleic acid initially present (initial nucleic acid) is measured (Step 1). Then, based on the initial concentration of nucleic acid thus measured, the number of copies of initial nucleic acid is calculated or estimated (Step 2) and the number of copies of nucleic acid to be sampled is determined (Step 3). When the number of copies of nucleic acid to be sampled is determined, if the number of copies of initial nucleic acid sample is larger than a predetermined value (that is, the number of copies of nucleic acid determined above), the initial sample is diluted. In contrast, if the number of copies of initial nucleic acid is smaller than the predetermined value, the initial sample is concentrated. In this manner, the concentration of the initial nucleic acid is adjusted to a favorable one for sampling (Step 4). Nucleic acid is taken just by a predetermined number of copies from the sample thus diluted or concentrated (Step 5) and added to a reaction solution (Step 6). The reaction solution is appropriately controlled (Step 7) and, if necessary, subjected to an amplification reaction (Step 8), and if not, subjected to a reaction for detecting nucleic acid (Step 9). The resultant sample obtained from the reaction is further subjected to detection or analysis for nucleic acid.

Figure 2:
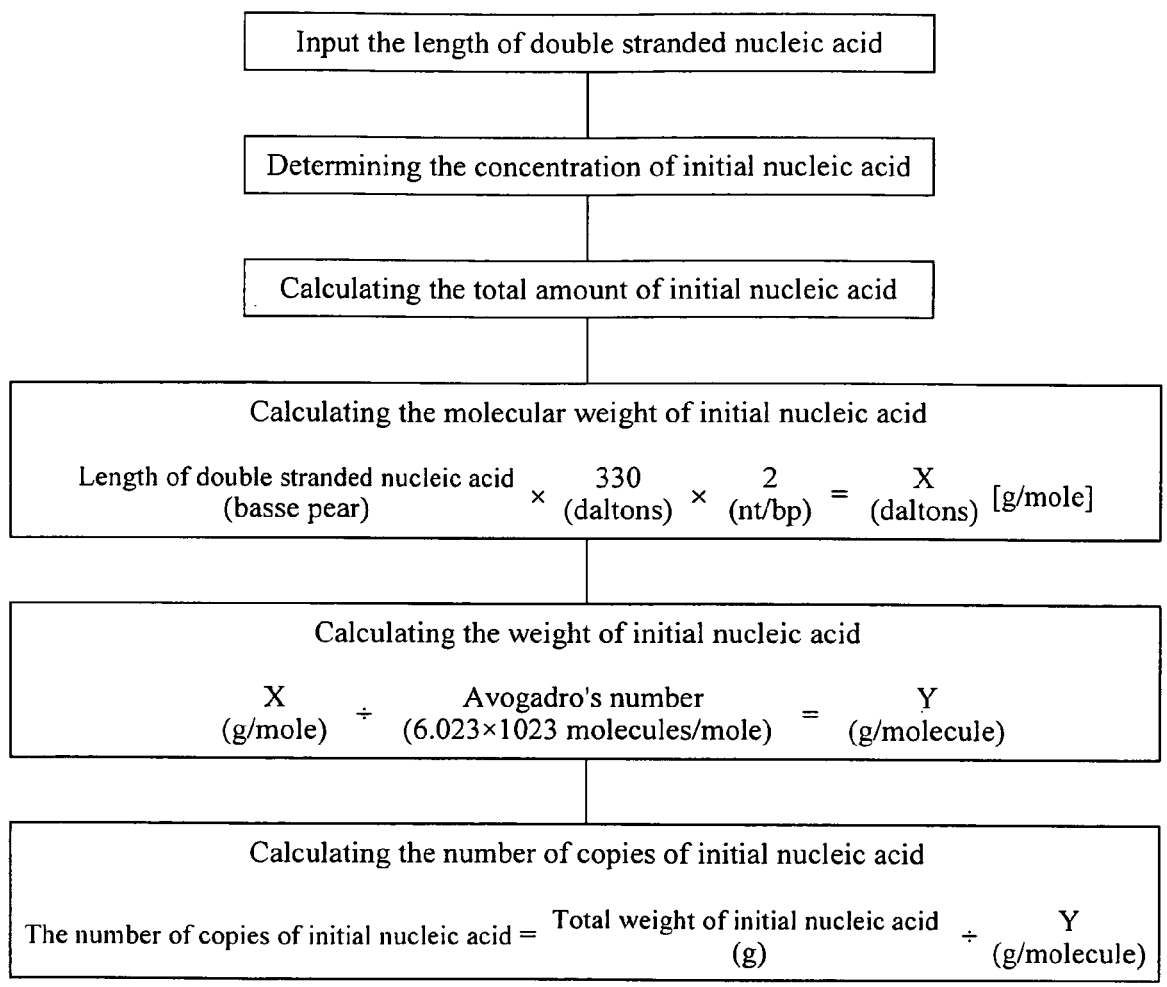
FIG. 2 is a flowchart showing a method of calculating the number of copies of initial nucleic acid.

FIG. 2 is a flowchart showing a method of calculating the number of copies of nucleic acid present in an initial nucleic acid sample. The length (the number of bases) of double stranded nucleic acid in the initial nucleic acid sample, nucleic acid concentration and the total weight of the nucleic acid are obtained. Based on these, the number of copies of initial nucleic acid is calculated in accordance with the instructions shown in FIG. 2.

Figure 3:
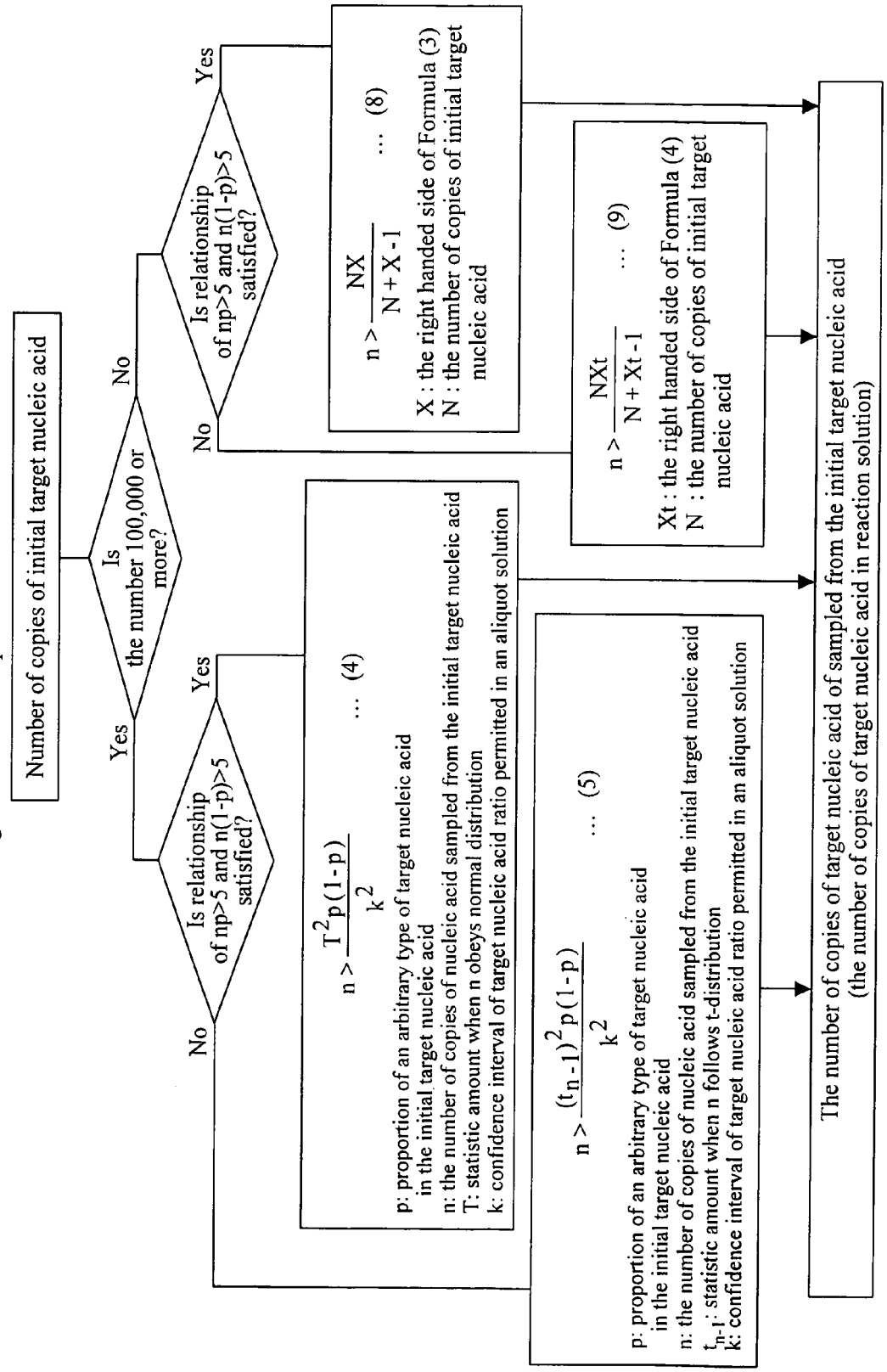
FIG. 3 is a flowchart showing a method of determining the number of copies to be sampled from target nucleic acid (the initial nucleic acid)

FIG. 3 shows a method of determining the number of copies of nucleic acid per sampling. Formulas (4), (5), (8) and (9) are the same as those shown in the section "DETAILED DESCRIPTION OF THE PREFERRED EMBODIMENTS". Using these Formulas, calculation method is shown with respect to the cases where the number of copies is less than 100,000 and 100,000 or more. If a more accurate calculation is required, Formula (1) obeying binomial distribution is employed. Note that the Formulas (2) to (14) (explained below) are defined as formulas approximated to the binomial distribution. More specifically, the principal of the binomial distribution may be applied to these formulas. If necessary, it may go without saying that Formulas (1) to (14) may be changed or modified.

Figure 4:
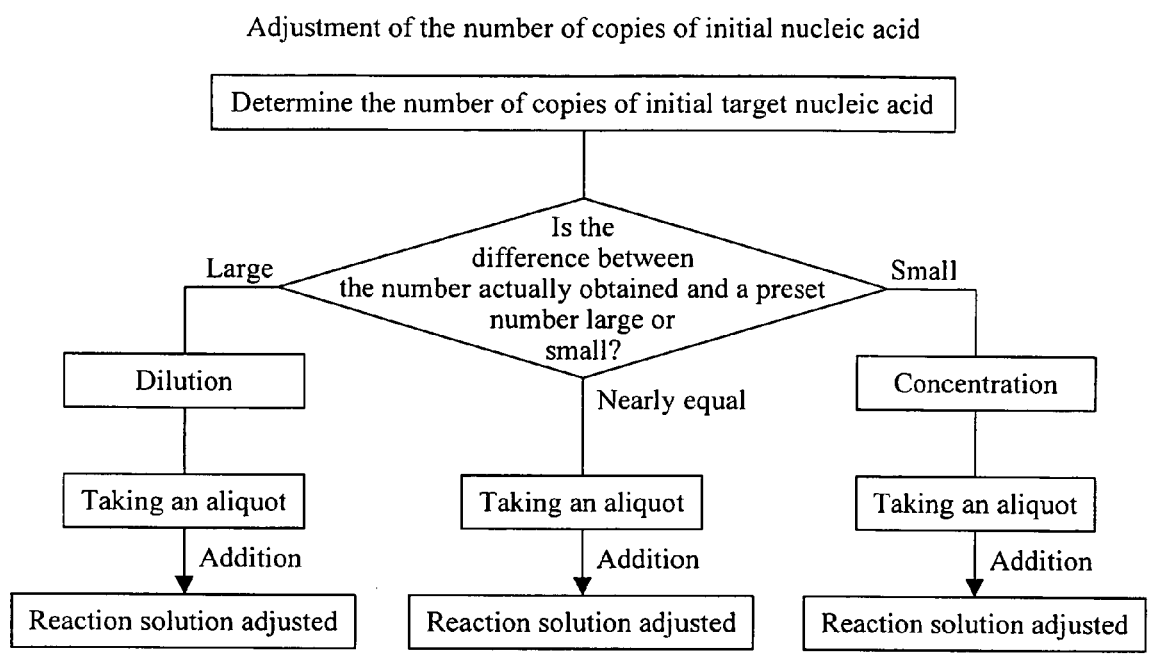
FIG. 4 is a flowchart showing a method of adjusting the number of copies of initial nucleic acid.

Furthermore, FIG. 4 shows a method of adjusting the number of copies of initial target nucleic acid depending on the number of copies of initial target nucleic acid, more specifically, the number of copies of initial target nucleic acid is smaller than, larger than or equal to that of the target nucleic acid to be sampled. If the number of copies of target nucleic acid to be sampled is substantially equal to that of the initial nucleic acid sample, the sample containing the initial target nucleic acid is directly used to prepare a reaction solution. When the number of copies of initial target nucleic acid in a sample is smaller than that to be sampled, the sample containing the initial nucleic acid is concentrated. Conversely, when the number of copies of initial target nucleic acid in a sample is larger than that to be sampled, the sample containing the initial target nucleic acid is diluted.

Figure 5:
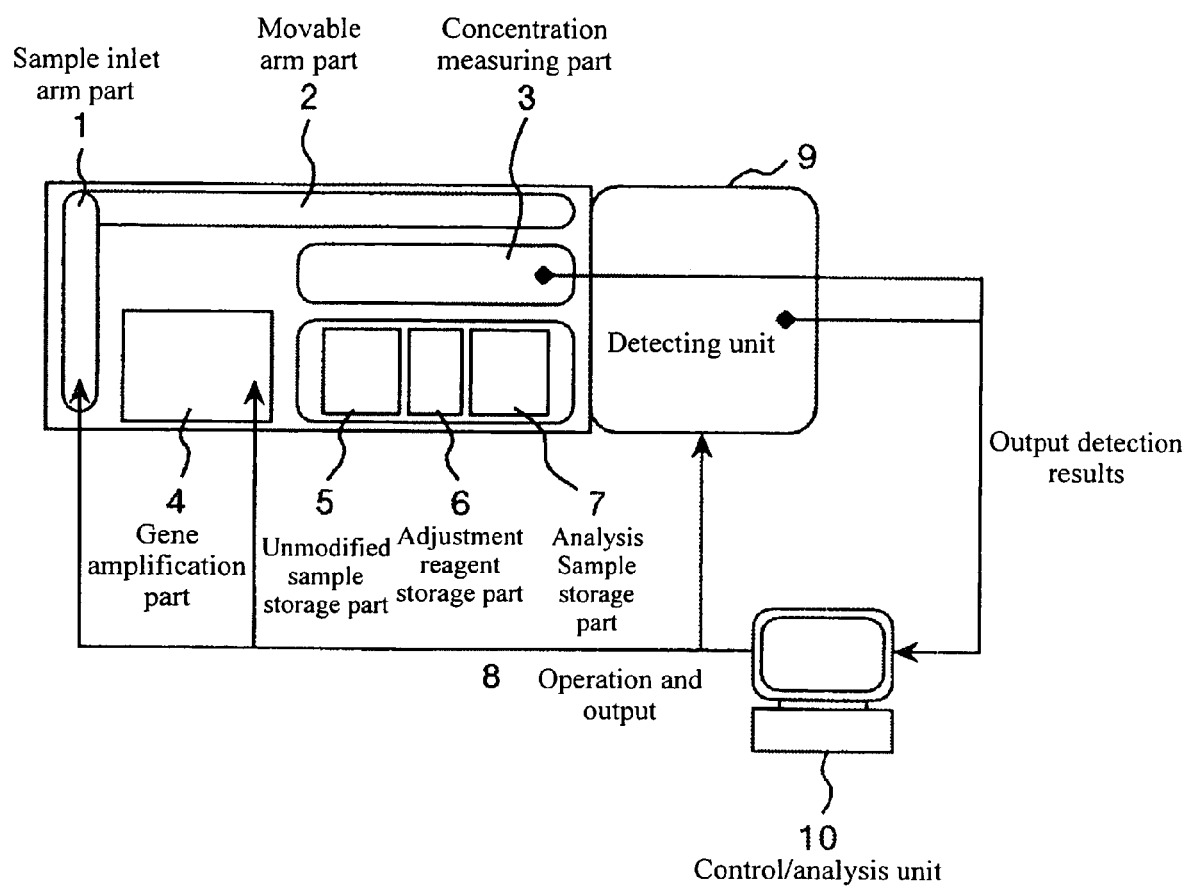
FIG. 5 is a schematic illustration showing the structure of an apparatus for detecting or analyzing nucleic acid, to which the preset invention is to be applied.
Figure 6:
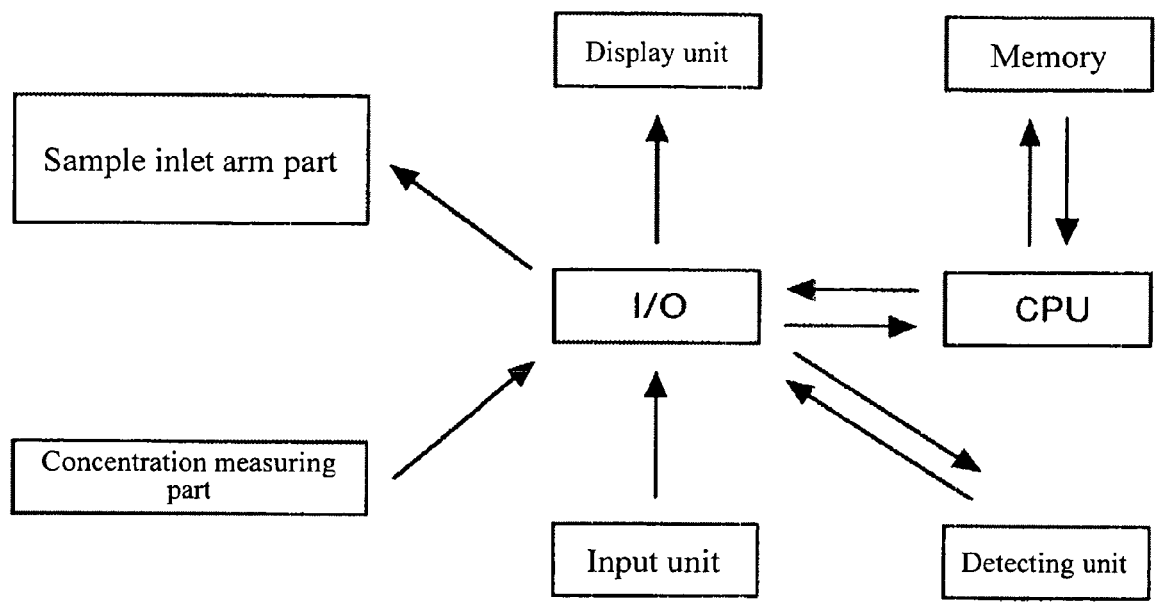
FIG. 6 is a schematic illustration showing a control/analysis unit of an apparatus for detecting or analyzing nucleic acid, to which the preset invention is to be applied, including other systems.

FIG. 5 is an illustration showing the structure of an apparatus for detecting or analyzing nucleic acid to be used in the present invention. A control/analysis unit controls a concentration measuring part, sample inlet arm part, gene amplification part and detecting unit. The apparatus also has a sample storage part and reagent storage part. FIG. 6 shows the relationship between the control/analysis unit of the apparatus for detecting or analyzing nucleic acid according to the present invention and other systems. When a measurement value of initial target nucleic acid measured in the concentration measuring part is input to the control/analysis unit, the number of copies of target nucleic acid to be sampled is determined based on the measurement value in the unit. Then, the control/analysis unit operates the sample inlet arm part so as to sample the determined number of copies of target nucleic acid. The control/analysis unit further controls operations of the later steps, that is, operations carried in the gene amplification part and the detecting units. A memory, which is a medium readable by a computer, stores a program (described later). A series of operations is executed under the control of the computer. (CPU). Furthermore, the operator inputs necessary instructions and conditions through an input unit. Operational results, present state and warning are displayed on a display unit. Based on these results shown in the display unit, the operator instructs the detection unit to detect nucleic acid and the display unit to display necessary information. More specifically, the present invention provides an apparatus for detecting or analyzing nucleic acid, comprising a sample-dispensing unit;

a unit for measuring the concentration of nucleic acid in a sample;

an input/output unit;

a nucleic acid detecting unit;

a memory unit storing a program which allows a computer to function as a) means for inputting the length of initial target nucleic acid, based on which and the concentration of initial nucleic acid the number of copies of the initial nucleic acid is determined, or inputting initial conditions such as a source of the nucleic acid;

b) means for calculating the number of copies of initial target nucleic acid based on the measured concentration of initial nucleic acid; and c) means for determining the number of copies of target nucleic acid to be added to a reaction for analysis based on the number of copies of the initial target nucleic acid calculated, in detecting not less than two types of target nucleic acids having base sequences different in at least one base;

a computer reading out the program stored in the memory unit and controlling the detection or analysis apparatus; and a display unit for displaying at least calculation results.

A method of the present invention comprises amplifying not less than two types of initial target nucleic acids having base sequences different in at least one base simultaneously, analyzing a quantitative proportion of amplified nucleic acid at a target gene site of the target nucleic acid, thereby obtaining the amplified nucleic acid in the same quantitative proportion as that of the initial target nucleic acid. To be more specific, this method comprises the following steps (also shown in FIG. 1).

(1) measuring a concentration of the target nucleic acid;

(2) determining the number of copies of the initial target nucleic acid;

(3) determining the number of copies of target nucleic acid to be sampled from the initial target nucleic acid by means of statistical formula, and added to an amplification reaction solution;

(4) adjusting the amplification reaction solution for nucleic acid by diluting or concentrating the initial target nucleic acid such that the number of copies of the target nucleic acid present in the amplification reaction solution for amplifying the target nucleic acid, is set at a predetermined value;

(5) amplifying the nucleic acid; and (6) analyzing the nucleic acid and attaching a warning note or sign to a sample leaving a low number of copies of nucleic acid.

Note that the sample of initial target nucleic acid used in the present invention refers to that of nucleic acid extracted from a biological sample, a replicated nucleic acid thereof a part of the nucleic acid extracted from a biological sample containing a desired region, or artificially synthesized nucleic acid. The biological sample refers to a sample such as cells, normal tissues, blood, cells contained in urine and tumor cells themselves taken from various organisms. The tumor cells can be taken by a surgical operation or a biological test.

The method of extracting target nucleic acid is not particularly limited. A conventionally known method such as the phenol-chloroform extraction method or the QIAampDNA Blood mini kit (manufactured by the company Qiagen) may be used. Furthermore, nucleic acid can be extracted from cells present in urine, or otherwise, extracted from cells taken from the test-target tissue and cells present in urine. When the tissue is taken from a test subject, any tissue may be used as long as it is derived from the test subject and it provides cells containing nucleic acid, for example, a part of a biological specimen used in a clinicopathologic test may be used. When urine is taken from a test subject, any cells falling off into urine may be used as long as it can provide nucleic acid of the subject to be tested. Usually nucleic acid can be efficiently extracted from normal cells and/or tumor cells falling off by metabolism in urine by any one of the methods mentioned above.

Examples of an apparatus for determining the number of copies of nucleic acid include an absorption spectrochemical analyzer, fluorospectrophotometer, and ultraviolet wavelengths detector (UV detector), but not limited to these. Any apparatus may be used as long as the number of copies of nucleic acid can be determined.

When a polymerase chain reaction (PCR) is used as the method for amplifying of nucleic acid, examples of an apparatus for use in the method include a thermal cycler such as MJ Research (manufactured by the company MJ Research), but not limited to this. Any apparatus may be used as long as it can amplify nucleic acid by the PCR method. In such a nucleic acid amplification apparatus in accordance with the PCR method, nucleic acid is amplified by repeatedly heating and cooling a micro container filled with a reagent for controlling nucleic acid amplification. Alternatively, when nucleic acid amplification is performed at a constant temperature, for example, a thermo-heater and an incubator may be used, but not limited to these. However, any apparatus may be used as long as it can amplify nucleic acid.

Now, an important step of the flowchart shown in FIG. 1 will be more specifically explained.

In step 1), the concentration of initial target nucleic acid is measured, and the number of copies of the initial target nucleic acid is determined based on the length of the initial target nucleic acid. This step will be more specifically explained below. In this step, any calculation method is employed as long as the number of copies of the initial target nucleic acid can be calculated, and may not be limited to the specific examples described below.

The concentration of initial target nucleic acid is measured by use of the aforementioned nucleic acid concentration measuring apparatus. Examples of a measuring method preformed by use of such an apparatus include UV determination method and a fluorescent determination method but not limited to these. Any method may be used as long as it can determine the concentration of initial target nucleic acid.

In step 2), the number of copies of initial target nucleic acid can be calculated from the concentration obtained from measurement in accordance with a known method, for example, described in Bio-experiment illustrated 3 (p26 to 33) by inputting the number of bases of the initial target nucleic acid. When the number of copies of the initial nucleic acid is not easily determined, it can be estimated in accordance with a known method, for example, disclosed in JP Patent Publication (Kokai) No. 2001-314194. To explain more specifically, the number of copies of target nucleic acid contained in an amplification reaction solution before amplification can be estimated from the amount of nucleic acid during or after the amplification. However, a method for determining the number of copies of initial target nucleic acid is not limited to these examples. Any method may be used as long as the number of copies of initial target nucleic acid can be determined.

In step 3), the number of copies of initial target nucleic acid at least required for an analysis reaction or an amplification reaction is determined from the number of copies of initial target nucleic acid in accordance with a statistic formula. In short, the number of copies of initial target nucleic acid to be sampled is determined in step 3). Alternatively, the number of copies of initial target nucleic acid at least required for an amplification or analysis reaction solution is determined from the estimated number of copies of initial target nucleic acid, from the amount of initial target nucleic acid during amplification or after amplification, in accordance with a statistic formula. Hereinbelow, a method of determining the number of copies of nucleic acid present in an amplification or analysis reaction solution using a statistic formula will be more specifically explained below.

When a reaction solution for amplification is prepared by sampling a solution containing not less than two types of target nucleic acids present in low copy numbers, the ratio of individual target nucleic acids changes by sampling or dilution. Therefore, the principle of the present invention resides in avoiding such a phenomenon where the ratio of two types of nucleic acids present in an aliquot or a diluted solution changes from the original ratio thereof. Thus, if the total amount of nucleic acids of an initial target nucleic acid sample is regarded as 1, and the proportion of the nucleic acid to be analyzed is expressed by p, then the proportion of the other nucleic acid can be expressed by 1−p. This obeys binomial distribution. Accordingly, when n number of copies of nucleic acid is taken, the probability P(b) that nucleic acid of b number of copies used for analysis are contained in the sampling solution can be expressed by the following formula (1):

$$P(b) = \frac{n!}{b!(n-b)!} p^b (1-p)^{n-b} \tag{1}$$

where,

P(b): the provability of containing b number of copies in an aliquot;

p: the proportion of one type of target nucleic acid in the initial target nucleic acid;

n: the number of copies of nucleic acid sampled from the initial target nucleic acid;

b: the number of copies of nucleic acid contained in the aliquot and subjected to analysis.

Provided that the number of copies of nucleic acid to be sampled is expressed by n, and n satisfies the relationship: np>5 and n(1−p)>5, the case approximately follows a normal distribution where an average is p, variance is p(1−p)/n. Therefore, the copy number of target nucleic acid to be sampled can be statistically obtained as described below.

Provided that a target nucleic acid solution contains a plurality of types of target nucleic acids where the number N of copies of initial target nucleic acid is sufficiently large, preferably N>100,000, when a certain type of target nucleic acid is present in a proportion of p, then n number of copies of this target nucleic acid is sampled from the target nucleic acid solution, then the ratio R of the target nucleic acid present in the aliquot (of the target nucleic acid) fall within the range represented by Formula (2) where T is the amount of statistics, np>5 and n(1−p)>5, in the confidence interval of a certain degree of confidence. Preferably T=1.96 is given at a 95% degree of confidence, more preferably T=2.58 is given at a 99% degree of confidence. When another degree of confidence is used, the amount of statistics T may be obtained from the normal distribution table.

$$p - T\sqrt{p(1-p)/n} < R < p + T\sqrt{p(1-p)/n} \tag{2}$$

where, p: the proportion of one type of target nucleic acid in the initial target nucleic acid;

n: the number of copies of nucleic acid sampled from the initial target nucleic acid;

T: the amount of statistics when n approximately obeys normal distribution;

R: Confidence interval of p (the possible range of p).

If the condition: np>5 and n(1−p)>5 is not satisfied, the possible range of R can be expressed by Formula (3) where amount of statistics of t distribution is represented by $t_{n-1}$ and more preferably, by Formula (1) following binomial distribution.

$$p - t_{n-1}\sqrt{p(1-p)/n} < R < p + t_{n-1}\sqrt{p(1-p)/n} \tag{3}$$

where, p, n, R are the same as defined in Formula (2).

$t_{n-1}$: the amount of statistic when n approximately obeys t distribution.

From Formulas (2) and (3), when the number of copies of initial target nucleic acid is sufficiently large, the possible value of R, if it is shown in terms of percentage with 95% degree of confidence, in place of showing in terms of the number of copies, are as shown in Table 1.

[Table 1]

TABLE 1

Relationship between number n and 95% confidence interval

| Number of copies | p value | | | | | | | | | |
|---|---|---|---|---|---|---|---|---|---|---|
| | 0.1 | | 0.2 | | 0.3 | | 0.4 | | 0.5 | |
| | Lower limit | Upper limit | Lower limit | Upper limit | Lower limit | Upper limit | Lower limit | Upper limit | Lower limit | Upper limit |
| 4 | −19.4 | 39.4 | −19.2 | 59.2 | −14.9 | 74.9 | −8.0 | 88.0 | 1.0 | 99.0 |
| 6 | −14.0 | 34.0 | −12.0 | 52.0 | −6.7 | 66.7 | 0.8 | 79.2 | 10.0 | 90.0 |
| 9 | −9.6 | 29.6 | −6.1 | 46.1 | 0.1 | 59.9 | 8.0 | 72.0 | 17.3 | 82.7 |
| 16 | −4.7 | 24.7 | 0.4 | 39.6 | 7.5 | 52.5 | 16.0 | 64.0 | 25.5 | 74.5 |
| 35 | 0.1 | 19.9 | 6.7 | 33.3 | 14.8 | 45.2 | 23.8 | 56.2 | 33.4 | 66.6 |
| 50 | 1.7 | 18.3 | 8.9 | 31.1 | 17.3 | 42.7 | 26.4 | 53.6 | 36.1 | 63.9 |
| 100 | 4.1 | 15.9 | 12.2 | 27.8 | 21.0 | 39.0 | 30.4 | 49.6 | 40.2 | 59.8 |
| 1000 | 8.1 | 11.9 | 17.5 | 22.5 | 27.2 | 32.8 | 37.0 | 43.0 | 46.9 | 53.1 |
| 10000 | 9.4 | 10.6 | 19.2 | 20.8 | 29.1 | 30.9 | 39.0 | 41.0 | 49.0 | 51.0 |

Table 1 means that statistically significant difference cannot be found in the 95% confidence interval sandwiched between the upper limit and the lower limit. Therefore, the narrower the interval, the higher the statistic probability of obtaining amplified nucleic acids at the same ratio as that of the initial target nucleic acids. From this, provided that the condition: np>5 and n(1−p)>5 is satisfied and a confidence interval is always permitted by a ratio of k, a predetermined-value, n can be expressed by Formula (4) where T is the amount of statistics. Preferably, the amount of statistics, T=1.96, is given at a 95% degree of confidence, more preferably, the amount of statistics, T=2.58, is given at a 99% degree of confidence. When other degree of confidence is employed, the amount of statistics, T may be obtained from the normal distribution table.

$$n > \frac{T^2 p(1-p)}{k^2} \quad (4)$$

where, p, n, T: the same as defined in Formula (2);

k: confidence interval of possible target nucleic acid ratio in an aliquot solution.

When the condition: np>5 and n(1−p)>5, is not satisfied, a predetermined value n can be preferably expressed by Formula (5) where the amount of statistics of t distribution is represented by $t_{n-1}$, and more preferably expressed by Formula (1) following binomial distribution.

$$n > \frac{(t_{n-1})^2 p(1-p)}{k^2} \quad (5)$$

where, p, n: the same as defined in Formula (2);

$t_{n-1}$: the same as defined in Formula (3);

k: the same as defined in Formula (4).

When the number of copies of initial target nucleic acid is low, the number of copies of the initial target nucleic acid is expressed by N. In this case, if Formula (2) and (3) are multiplied by a correction term of finite population, Formula (2) can be expressed by Formula (6), and Formula (3) can be expressed by Formula (7).

$$p - T\sqrt{p(1-p)/n} \times \sqrt{\frac{N-n}{N-1}} < R < p + T\sqrt{p(1-p)/n} \times \sqrt{\frac{N-n}{N-1}} \quad (6)$$

$$p - t_{n-1}\sqrt{p(1-p)/n} \times \sqrt{\frac{N-n}{N-1}} < \quad (7)$$

$$R < p + t_{n-1}\sqrt{p(1-p)/n} \times \sqrt{\frac{N-n}{N-1}}$$

where, p, n, T, R: the same as defined in Formula (2);

$t_{n-1}$: the same as defined in Formula (3);

N: the number of copies of initial target nucleic acid.

Therefore, when the number of copies of the initial target nucleic acid is statistically low, preferably, smaller than 100,000, the number of copies of the initial target nucleic acid is represented by N. In this case, if the condition: np>5 and n(1−p)>5, is satisfied in the confidence interval of a certain degree of confidence, the predetermined value n in the present invention can be expressed by Formula (8) where the right-handed side represented by Formula (4) is represented by X. Preferably, the amount of statistics, T=1.96, is given at a 95% degree of confidence, and more preferably, the amount of statistics, T=2.58, is given at a 99% degree of confidence. Furthermore, when another degree of confidence is set, the amount of statistics T may be obtained from the normal distribution table.

$$n > \frac{NX}{N+X-1} \quad (8)$$

where,

X: the right-handed side of Formula (4);

N: the same as defined in Formula (6) and (7).

When the condition: np>5 and n(1−p)>5, is not satisfied in a confidence interval of a certain degree of confidence, the predetermined n can be expressed by Formula (9) where the right handed side of Formula (5) is represented by Xt, and more preferably calculated in accordance with formula (1) obeying binomial distribution.

$$n > \frac{NXt}{N + Xt - 1} \quad (9)$$

where,

Xt: the right-handed side of Formula (5);

N: the same as defined in Formula (6) and (7).

Furthermore, the lowest number of copies of initial target nucleic acid, which is required for amplifying a target gene present in a smaller proportion without fail, can be calculated. To explain more specifically, as is apparent from Table 1, when a certain type of target gene present in a proportion of 10% in a plurality of types of target nucleic acids having not less than 100,000 copies is amplified, if the number of copies is less than 35, the target gene may not be detected at a 95% degree of confidence in some cases. Therefore, a predetermined value n to be sampled for amplifying the target nucleic acid contained in a proportion of p without fail in the confidence interval of a certain degree of confidence is desirably given by Formula (10) given by the Poisson distribution, provided that the probability of containing the number b of copies in the aliquot is expressed by P(b).

$$P(b) = \frac{(np)^b}{b!} e^{-np} \quad (10)$$

where,

P(b), p, n, b: the same as defined in Formula (1);

e is the bottom of natural logarithm.

However, Formula (10) is complicated and difficult. Therefore, the binomial distribution is desirably approximated to normal distribution. If so, a predetermined value n for amplifying the target nucleic acid contained in a proportion of p, without fail in the confidence interval of a certain degree of confidence can be expressed by Formula (11) where T is the amount of statistics. Preferably T=1.96 is given at a 95% degree of confidence, more preferably T=2.58 is given at a 99% degree of confidence. When another degree of confidence is used, the amount of statistics T may be obtained from the normal distribution table; however, more preferably, from the Poisson distribution.

$$n > \frac{T^2(1-p)}{p} \quad (11)$$

where, p, n, T: the same as defined in Formula (2).

When the condition: np>5 and n(1−p)>5, is not satisfied, the predetermined value n can be obtained by Formula (12) where the amount of statistics of t distribution is represented by $t_{n-1}$, and more preferably, the Poisson distribution is used.

$$n > \frac{(t_{n-1})^2(1-p)}{p} \quad (12)$$

where, p, n, T: the same as defined in Formula (2).

When the number of copies of initial target nucleic acid is low, if the number of copies of the initial target nucleic acid is represented by N and the right hand side of Formula (11) is represented by Y, the predetermined value n can be expressed by Formula (13).

$$n > \frac{NY}{N + Y - 1} \quad (13)$$

where,

Y: the right-handed side of Formula (11);

N: the same as defined in Formulas (6) and (7).

When the condition: np>5 and n(1−p)>5, is not satisfied, if the right hand side of Formula (12) is represented by Y, the predetermined value n can be expressed by Formula (14), and more preferably, the Poisson distribution is used.

$$n > \frac{NYt}{N + Yt - 1} \quad (14)$$

where,

Yt: the right-handed side of Formula (12);

N: the same as defined in Formulas (6) and (7).

Preferably T=1.96 is given at a 95% degree of confidence, more preferably T=2.58 is given at a 99% degree of confidence. When another degree of confidence is set, the amount of statistics T may be obtained from the normal distribution table.

By the methods mentioned above, in amplifying not less than two types of target nucleic acids having base sequences different in at least one base simultaneously by using primers, the amount of nucleic acid amplified is proportional to the amount of the target nucleic acid. Furthermore, in the value p and k of Formulas (4), (5), (8) and (9) according to the present invention vary depending upon the detection method and detection apparatus to which the present invention is applied. However, in the case of an analytical method and apparatus poor in quantitativeness, value k is preferably set to be high whereas value k is preferably set to be low in the case of an analytical method and apparatus high in quantitativeness. Value P is set based on the proportion of the target nucleic acid to be detected. However, when the proportion is unknown, value p is preferably set at 0.5, and more preferably, set at an estimated proportion. The detection method and apparatus to which the present invention can be possibly applied and values p and k will be more specifically explained in step 5) (described later).

In step 7), the number of copies of target nucleic acid present in an amplification reaction solution or an analysis reaction solution is adjusted. A method of adjusting the number of copies of target nucleic acid in an amplification reaction solution or an analysis reaction solution to the value determined in the aforementioned methods will be described in detail below. This step is satisfactorily performed if the number of copies of the target nucleic acid in an amplification or analysis reaction solution is adjusted at the value determined by the aforementioned method and not limited by the following detailed description.

As a result of determining the number of copies of initial target nucleic acid, if the number of copies of the initial target nucleic acid is sufficiently large, the initial target nucleic acid must be diluted by sampling the initial target nucleic acid and adding to a solvent. Any solvent may be used for dilution as long as it dissolves a nucleic acid fragment and it does not affect the nucleic acid amplification reaction or nucleic acid analysis reaction. In contrast, if the number of copies of the initial target nucleic acid is not more than a predetermined number of initial target nucleic acid, the initial target nucleic acid can be concentrated by a known method such as the ethanol precipitation method.

When nucleic acid is amplified in the next step, a diluted or concentrated initial target nucleic acid solution adjusted in copy number is sampled and added to a nucleic acid amplification reagent (reaction) solution prepared separately such that the number of copies of initial target nucleic acid is consistent with the predetermined number of copies determined by the aforementioned method. When the number of copies of initial target nucleic acid determined is low enough to directly adjust, the initial target nucleic acid may be sampled and added to a solution preparation containing the nucleic acid amplification reagent (reaction) solution and a primer(s) such that the target nucleic acid is contained in an amount of a predetermined number determined in the aforementioned method. In contrast, when the number of copies of initial nucleic acid does not reach the predetermined value, a test sample is added or concentrated, or otherwise, is not subjected to analysis. Alternatively, a warning note or signal may be attached after analysis.

When the initial target nucleic acid is directly analyzed without amplifying it, the aforementioned diluted or concentrated initial target nucleic acid solution adjusted in copy number is sampled and added to a reaction solution for analysis. Furthermore, when the number of copies of initial target nucleic acid determined is low enough to directly add, the target nucleic acid is sampled to add to a reaction solution for analysis such that the target nucleic acid is contained in the predetermined value determined by the aforementioned method. The reaction solution for analysis may contain any components as long as a predetermined analysis of the initial target nucleic acid can be performed.

In step 8), nucleic acid is amplified. When the analysis is directly performed without amplifying nucleic acid, this step is not required. The operation goes to step 9). Now, amplification of the nucleic acid performed in this step will be more specifically explained. However, a step can be satisfactorily performed in any manner as long as nucleic acid can be amplified and may not to be limited to the following specific examples.

The method of amplifying nucleic acid is not particularly limited. Examples of such a method include the PCR method, strain displacement amplification (SDA) method, method of isothermal amplification of genes (ICAN), and loop-mediated isothermal amplification (LAMP) method. Any method may be used as long as not less than two types of target nucleic acids having base sequences different in at least one base can be simultaneously amplified by primers; however, the PCR method is preferably used. When the PCR method is used for amplifying nucleic acid, the repeating times of a PCR cycle must be determined. In the present invention, the PCR cycle may be repeated any times as long as a nucleic acid fragment can be amplified; however, the cycle is preferably repeated about 20 to 40 times.

The nucleic acid amplification reagent to be used in the present invention is not limited. As long as nucleic acid is amplified, any reagent may be used. The primer is designed to have a gene sequence (base sequence) specific to a part of a desired nucleic acid sequence to be detected. The primer may be designed in any manner as long as it can be amplified by a nucleic acid amplification method. To facilitate the detection of an amplified nucleic acid fragment, the primers may be labeled as described later, or nucleic acid can be amplified by use of labeled bases (e.g., bases labeled with radioactive phosphorus). Alternatively, a nucleic acid fragment may be labeled after the nucleic acid is amplified. The labeling method is not particularly limited as long as detection can be easily performed. Examples of a label used in such a labeling method include radioactive substance, fluorescent substance, chemical luminescent substance, and biotin (which is detected avidin labeled with an enzyme). A primer may be labeled in advance with, for example a fluorescent dye such as an A.L.F red (Cy5, trade name) amidite reagent (manufactured by the company Pharmacia) at its end. Furthermore, as a fluorescent label, FAM, TET, HEX, TAMRA, ROX (all are trade names, manufactured by the company Applied Bio systems) may be used. In these cases, either one of the 5' terminal and 3' terminal may be labeled, preferably the 5' terminal is labeled.

In step 10), target nucleic acids are analyzed and the quantitative ratio of two different target nucleic acids are determined. Examples of a method for detecting not less than two types of nucleic acids having different sequences contained in an amplification or analysis reaction solution include the single strand conformation polymorphism analysis (SSCP method), dichromatic fluorescent DNA array method, Mass array method, Invader method, and Bamper method, but not limited to these. Any method may be used as long as desired target nucleic acid can be detected in a solution containing SNPs, two different allelic genes, and/or a plurality of different nucleic acids.

The single strand conformation polymorphism analysis (SSCP method) is performed by amplifying nucleic acids homologous to each other but containing the site different in at least one base, denaturing the resultant nucleic acids amplified, distinguishing the difference in base sequence in terms of conformational difference, and electrophoretically detecting the conformational difference based on quantitative ratio of two different peaks. As a clinical test method employing this analysis, a loss of heterozygosity (LOH) method and a microsatellite instability (MSI) method may be mentioned.

In the case of analysis in which detecting and determining can be made based on a quantitative ratio such as area ratio or height ratio between two different peaks, the quantitative ratio detected or determined must have a higher correspondency with the initial nucleic acid and higher quantitativeness is required. In this case, generally the quantitativeness within 10% is required in the confidence interval (difference between the upper limit and the lower limit) and k=0.05 can be provided.

In the nucleic acid array method using two kinds of fluorescent dye (dichromatic fluorescent DNA array method), difference between DNA molecules is detected based on a change of fluorescent dye to red or green. Therefore, it is principally difficult to perform quantitative determination and generally detection can be roughly made in this method. Examples of a detection method employing such an analysis include a Comparative Genomic Hybridization (CGH) method and various types of SNP detection methods. In this case, the quantitativeness within about 30% confidence interval is required and k=0.15 can be provided. Furthermore, to analytically confirm that a target nucleic acid is a heterozygote, the ratio of two different target nucleic acids contained in the initial nucleic acid is 1:1. Therefore, p=0.5 can be provided.

Examples of an apparatus for use in detecting and analyzing amplified nucleic acid include the capillary electrophoresis apparatus, gel-plate electrophoresis, mass spectrometric apparatus, and nucleic acid micro array. Specific examples include, but not limited to, a genetic analyzer (manufactured by the company ABI) for determining the base sequence of nucleic acid; a capillary electrophoretic system (manufactured by the company Agilent Technologies) capable of analyzing various substances such as metal ions, nucleic acids and proteins; CE/MS system (manufactured by the company Agilent Technologies), which is a combination system between capillary electrophoresis and mass spectrometry; Base station (trade name) 100 DNA fragment analyzer (manufactured by the company MJ Research) for determining the sequence of nucleic acid by use of a gel plate, microflex (manufactured by the company BrukerDaltonics) capable of capturing difference in bases of polymorphism in a gene as difference in mass; and a nucleic acid microarray in which synthesized probes having a base sequence of a desired gene region to be detected are aligned onto a chip and the nucleic acid to be detected is allowed to react with the chip. Any apparatus may be used as long as it detects the nucleic acid to be detected.

More specifically, analysis is preformed by determining loss of heterozygote by use of the SSCP method using an electrophoresis apparatus with 16 capillaries. The analysis in the present invention is satisfactory as long as "the predetermined value" can be determined by using Formulas (4), (5), (8) and (9) and amplification of the target nucleic acid can be performed in a predetermined confidence interval with respect to the proportion of the target nucleic acid and thus not limited to the measuring method described later. As the result that the amplified nucleic acid is electrophoretically analyzed by the method mentioned above, one or two peaks can be obtained. LOH is determined by amplifying nucleic acid used as a standard and nucleic acid as a test-sample, measuring the heights of two peaks for each sample, calculating the ratio of the two peaks, calculating a reduction rate with respect to one of the two peaks, and comparing the difference in the reduction rate between test nucleic acid and the standard nucleic acid. When the difference is small, the test sample is determined as negative. In contrast, when the difference is large, the test sample is determined as positive. In the case where the difference is in the vicinity of the threshold previously determined, determination is made invalid.

The case where the number of copies of target nucleic acid is examined before amplification of nucleic acid, or the number of copies of target nucleic acid is examined during or after amplification and analysis is performed even if the number of copies of target nucleic acid is low will be described in detail. However, the step is satisfactory as long as a test-sample nucleic acid is determined to have a lower number of copies based on final measurement results and is not limited to the examples mentioned below.

When target nucleic acid having the number of copies not more than a predetermined number obtained by a statistic formula is amplified and subjected to analysis for LOH, the confidence interval of the obtained peaks can be obtained based on the number of copies of initial target nucleic acid and the number of copies of the target nucleic acid in an amplification reaction solution and the obtained peak ratio and in accordance with Formulas (2), (3), (6), and (7). The obtained confidence interval reaches the range including the threshold, there are two possibilities of the test results, that is, both positive and negative results. In this case, a warning note or sign for informing that "analysis was carried out using a low number of copies" is preferably attached to the test results. More preferably, this test results are treated as "indeterminant" or "impossible-to-determine" due to a low number of copies. In other cases where the confidence interval does not include the threshold, either positive or negative results are shown. More specifically, in both cases, a warning note or sign for informing the "analysis was carried out using a low number of copies" is preferably attached to the test results. As described, since the expansion of the confidence interval due to a low number of copies is reflected in the measurement results, more accurate measurement results can be obtained.

The present invention also provides a program for use in detecting not less than two types of target nucleic acids having base sequences different in at least one base. More specifically, the program includes the following means for allowing a computer to function to analyze not less than two types of the target nucleic acids having base sequences different in at least one base by not less than two primers specific to the sites of base sequences different in at least one base or not less than two types of primers specific to the sites of base sequences mutually different:

a) means for inputting, as initial conditions, the length of the initial target nucleic acid for determining the number of copies of the initial target nucleic acid based on the concentration of nucleic acid or a source of the nucleic acid;

b) means for calculating the number of copies of the initial target nucleic acid based on the result of measuring the concentration of the initial target nucleic acid;

c) means for determining the number of copies of target nucleic acid required for analysis reaction solution based on the number of copies of initial target nucleic acid thus calculated; and d) means for determining whether an initial target nucleic acid, in which the number of copies of the target nucleic acid in the analysis reaction solution cannot be adjusted to a predetermined value or more, is used for analysis or not by comparing the number of copies of initial target nucleic acid with the number of copies of target nucleic acid required for an analysis reaction; or determining that, when the initial target nucleic acid sample is used for analysis, analysis results are not used as data or used as data with a warning described for or a sign attached to the analysis data.

There is another program for use in simultaneously amplifying not less than two types of the target nucleic acids having base sequences different in at least one base by use of not less than two primers specific to the sites of base sequences different in at least one base or not less than two types of primers specific to the site of mutually different base sequence and subjected to analysis. This program includes the following means a) means for inputting, as initial conditions, the length of initial target nucleic acid for determining the number of copies of the initial target nucleic acid based on the concentration of initial target nucleic acid or a source of the nucleic acid.

b) means for calculating the number of copies of the initial target nucleic acid based on the result of measuring the concentration of the initial target nucleic acid;

c) means for determining the number of target nucleic acid required in an amplification reaction solution based on the number of initial target nucleic acid thus calculated; and d) means for comparing the number of copies of initial target nucleic acid and the number of copies of target nucleic acid required for an amplification reaction.

Furthermore, in the method of simultaneously amplifying not less than two types of the target nucleic acids having base sequences different in at least one base by use of not less than two primers specific to the sites of base sequences different in at least one base or not less than two types of primers specific to the site of base sequence mutually different analyzing the quantitative ratio of amplified nucleic acids of a target gene site in the target nucleic acid, comparing the ratio of the target nucleic acid used as a standard and target nucleic acid as a test substance, and determining whether the peak ratio changes or not based in the threshold previously determined, a program having the following means is provided.

a) means for demanding, as initial conditions the length of initial target nucleic acid for determining the number of copies of the initial target nucleic acid based on the concentration of initial target nucleic acid or a source of the nucleic acid;

b) means for calculating the number of copies of the initial target nucleic acid based on the concentration of the initial target nucleic acid determined by means of a nucleic acid concentration measuring apparatus or based on the results estimated from the amplification amount of nucleic acid during or after the amplification reaction;

c) means for calculating the confidence interval with respect to the results obtained from the analysis for the proportion of target nucleic acids by use of the binomial distribution or its approximate equation; and d) means for checking whether the threshold for use in determination is overlapped with the confidence interval and determining whether a significant difference is present or not depending upon whether the threshold is overlapped with the confidence interval or not, and determining "impossible-to-determine" in the case where the threshold is overlapped with the confidence interval.

Furthermore, there is provided a recording medium, in which the program mentioned above is recorded, readable by a computer.

Example 1

Determination of the proportion of heterozygote allelic gene in nucleic acid present in a low concentration by SSCP analysis 1. Sample Preparation and SNP Amplification In obtaining the proportion of allelic genes present in nucleic acid extracted from human blood, more specifically, a relative ratio of two allelic genes contained in initial target nucleic acid and that after amplification, the number of copies of initial target nucleic acid required for analysis performed (A) within an accuracy of 2%, (B) within an accuracy of 5%, (C) within an accuracy of 15%, and (D) within an accuracy of 40% are shown in Table 2. Four types of target nucleic acid amplification solutions containing the number of copies of initial target nucleic acid corresponding to the aforementioned four cases were prepared in accordance with the formulation shown in Table 3. As is apparent from Table 2, the higher the accuracy, the larger the number of copies of initial target nucleic acid. Preparation was performed by repeating a trial 8 times.

[Table 2]

TABLE 2

Number of copies of initial target nucleic acid

| | Case | | | |
|---|---|---|---|---|
| | A | B | C | D |
| Copy number | 20000 | 2000 | 200 | 20 |

TABLE 3

Composition of nucleic acid amplification reagent

| Reagent | Final concentration |
|---|---|
| TrisHCl (pH8.3) | 10 mM |
| KCl | 50 mM |
| MgCl | 1.5 mM |
| dATP, dTTP, dCTP, dGTP | 0.2 mM for each |
| Primer Forward Chain | 0.5 µM |
| Primer Reverse Chain | 0.5 µM |
| Nucleic acid amplification enzyme | 0.75 Units |

Each preparation solution was subjected to PCR amplification targeting an SNP site of a heterozygotic allelic gene. PCR amplification was performed by repeating 30 times a cycle consisting of a denaturation reaction at 95° C. for 2 minutes, a reaction at 95° C. for 30 seconds, a reaction at 57° C. for 30 seconds and a reaction at 72° C. for 30 seconds, and thereafter, performing an elongation reaction at 72° C. for 7 minutes.

2. SSCP Analysis

After the amplification reaction, the obtained PCR product was subjected to blunt end treatment at 37° C. for 30 minutes by use of Klenow Fragment (manufactured by Takara Bio Inc.) in a reaction mixture shown in Table 4.

[Table 4]

TABLE 4

Composition of reaction mixture for blunt end treatment

| Component | Volume |
|---|---|
| Klenow Fragment | 1.0 Unit |
| PCR product | Unmodified solution 5 µl |
| Total volume | 6 µl |

After completion of the blunt end treatment, a reaction mixture for SSCP analysis was prepared by mixing the sample, TAMRA size standard (manufactured by the company ABI), and Formamid (manufactured by the company ABI), in accordance with the formulation shown in Table 5. After heat denaturation was performed at 92° C. for 2 minutes, the SSCP analysis was performed in the conditions shown in Table 6.

[Table 5]

TABLE 5

Formulation of reaction solution for SSCP analysis

| Component | Volume |
|---|---|
| Blunt ended sample product | 3.0 µl |
| TAMRA Size Standard | 1.0 µl |
| Formamid | 36 µl |
| Total volume | 40 µl |

TABLE 6

Condition of SSCP analysis

| Start-up voltage: | 20 kV |
|---|---|
| Start-up time: | 5 sec |
| Voltage for electrophoresis: | 15 kV |
| Detection time: | 45 min |

3. Relative Ratio of Allelic Gene

In the SSCP analysis, the amplification amount of heterozygotic allelic genes can be chromatographically detected in the form of two waves. A change of the allelic genes after nucleic acid amplification, which were principally present in the same amount, can be checked by obtaining the relative ratio of the two waves. The change in peak ratio was checked by repeating the experiment 8 times. The results are shown in Table 7.

[Table 7]

TABLE 7

| | Change of proportion of one of two allelic genes | | | |
|---|---|---|---|---|
| ALD | A | B | C | D |
| 1 | 49.9 | 49.6 | 48.7 | 56.7 |
| 2 | 51.3 | 51.5 | 49.4 | 51.7 |
| 3 | 50.2 | 50.3 | 50.3 | 58.8 |
| 4 | 50.5 | 50.0 | 54.8 | 59.4 |
| 5 | 49.7 | 48.7 | 48.6 | 54.1 |
| 6 | 49.8 | 49.5 | 46.9 | 38.5 |
| 7 | 50.4 | 50.2 | 46.2 | — |
| 8 | 49.9 | 49.8 | 50.3 | — |
| Max-Min | 1.6 | 2.7 | 8.6 | 20.9 |

—: No amplification of nucleic acid was observed.

In the result of Table 7, the range of variation between experiments was narrow since the experiment was not repeated so many times. However, the tendency that the lower the number of copies, the wider the range of variation was definitely observed. As is apparent from the results, analysis can be made within the range of a desired accuracy by controlling an amount of nucleic acid sampled from the initial target nucleic acid.

Example 2

LOH Examination by SSCP Analysis

1. Determination of Analysis Condition

The LOH examination is performed by determining the quantitative ratio of two different allelic genes in nucleic acid by using a single base difference in the nucleic acid and comparing the quantitative ratio with that of a predetermined target nucleic acid used as a standard to investigate a change in quantitative ratio. To explain more specifically, the quantitative ratio of two different allelic genes in animal genomic nucleic acid is generally 1:1. When one of two different allelic genes is detected, since the proportion of the initial target nucleic acid to be detected is deemed as 50%, p=0.5 is given. However, whether the quantitative amount ratio (proportion) of the allelic gene (test object) changes or not is not determined until analysis is completed. Therefore, the same value as in the standard, p=0.5 is provisionally given and corrected after the analysis. In the analysis performed in this example, since nucleic acid of 10% or more must be detected, in other words, since the confidence interval must be set within 10% (±5%) with a 95% degree of confidence, so that T=1.96 and k=0.05 were given:

In this example, nucleic acid extracted from the blood taken from a patient was used as a standard initial target nucleic acid, whereas nucleic acid extracted from the tumor tissue and urine of the patient was used as an initial target nucleic acid of a test-sample. Test was performed by amplifying 10 types of test regions of a gene.

2. Determination of Copy Number of Initial Target Nucleic Acid and Determination of Copy Number of Target Nucleic Acid in Amplification Reaction Solution Nucleic acid was extracted from human blood of a patient having bladder cancer in accordance with the phenol/chloroform extraction method and used as a standard initial nucleic target nucleic acid. Whereas, nucleic acid was extracted from human urine of the patient in accordance with the same method as above and used as an initial target nucleic acid of a test sample. The concentrations of these initial target nucleic acids were measured by use of UV absorption apparatus. The number of copies was calculated by assuming that the length of genomic DNA per cell was $4.0 \times 10^6$ kbp. The numbers of copies are shown in Table 8.

[Table 8]

TABLE 8

| | Concentration of initial target nucleic acid and the number of copies | | |
|---|---|---|---|
| Genomic DNA | DNA concentration (µg/µl) | Number of copies/µl | Total number of copies |
| Genomic DNA derived from blood | 5.0 | $1.05 \times 10^6$ | $5.25 \times 10^7$ |
| Genomic DNA derived from tissue | 0.1 | $2.1 \times 10^4$ | $2.1 \times 10^6$ |
| Genomic DNA derived from urine | 0.0005 | 105 | 1575 |

In the cases of genomic DNA derived from blood and tissue, a parent population is considered sufficiently large since not less than 100,000 copies are present. Therefore, the number of copies of target nucleic acid in an amplification reaction solution was calculated in accordance with Formulas (4) and (5). Conversely, in the case of genomic DNA derived from urine herein, the initial number of copies was low. Therefore, the number of copies of target nucleic acid in an amplification reaction was calculated in accordance with Formulas (8) and (9) by giving the initial copy number, N=1575. As is described above, the number of copies (shown in Table 9) required for an amplification reaction was given.

[Table 9]

TABLE 9

| Number of copies required for amplification of target nucleic acid | |
|---|---|
| Genomic DNA | Number of copies |
| Genomic DNA derived from blood | 385 |
| Genomic DNA derived from tissue | 385 |
| Genomic DNA derived from urine | 309 |

In this test, since 10 types of gene test regions were amplified, 10 types of reaction solutions were prepared. More specifically, to dispense the initial target nucleic acid having a requisite number of copies (requisite concentration) for amplification by an aliquot (1 µl) to each of the reaction solutions, at least 10 µl of initial target nucleic acid must be prepared. However, in the case where the total number of copies of genomic DNA is too low to satisfy the requisite amount for analysis, reliable test results may not conceivably be obtained. In this Example, to deal with this case, analysis was performed and then a warning note or sign for informing the reliability of the determination was attached to the final results.

3. Preparation of Nucleic Acid Amplification Reaction and Amplification of Nucleic Acid Target nucleic acid contained in a reaction solution is preferably present in a concentration of not less than a predetermined number of copies/μl of the reaction solution (shown in Table 9). When a sufficient number of copies of initial target nucleic acid is present, the concentration is preferably adjusted to about 10,000 copies/μl. Therefore, in the cases of genomic DNA derived from blood and tissue, a diluted solution having a concentration of 10,000 copies/μl was prepared, as shown in Table 10. In the case of genomic DNA derived from urine, to increase, even if only slightly, 15 μl of initial target nucleic acid solution was subjected to the ethanol precipitation to concentrate the solution up to 10 μl, that is, to a concentration of 157 copies/μl.

[Table 10]

TABLE 10

Number of copies contained in reaction solution of target nucleic acid

| Genomic DNA | Number of copies |
|---|---|
| Genomic DNA derived from blood | 10000 |
| Genomic DNA derived from tissue | 10000 |
| Genomic DNA derived from urine | 157 |

In this Example, nucleic acid was amplified by the PCR method. 10 types of amplification reaction solutions were prepared in accordance with compositions and concentrations shown in Table 11.

[Table 11]

TABLE 11

Composition of nucleic acid amplification reaction

| Composition | Final concentration |
|---|---|
| TrisHCl (pH8.3) | 10 mM |
| KCl | 50 mM |
| MgCl | 1.5 mM |
| dATP, dTTP, dCTP, dGTP | 0.2 mM for each |
| Primer Forward Chain | 0.5 μM |
| Primer Reverse Chain | 0.5 μM |
| Nucleic acid amplification enzyme | 0.75 Units |

To the amplification reaction solutions thus prepared, 1.0 μl of diluted or concentrated initial target nucleic acid was dispensed such that the number of copies of target nucleic acid in the amplification reaction corresponds to not less than values shown in Table 2, except for the case of nucleic acid derived from urine. PCR reaction was performed by repealing 30 times a cycle consisting of a denaturation reaction at 95° C. for 2 minutes, a reaction at 95° C. for 30 seconds, a reaction at 57° C. for 30 seconds and a reaction at 72° C. for 30 seconds, and thereafter, performing an elongation reaction at 72° C. for 7 minutes.

4. Determination of Peak Ratio by Using SSCP Analysis

To prepare a sample for the SSCP analysis, a reagent and a test sample (amplified DNA product) were added in the order shown below; however, the order of addition was not limited thereto. First, 36 μl of Formamid serving as a DNA denaturalizing argent was added to a micro-container for use in analysis. To this, 1.0 μl of 4 nM size marker, namely, TAMRA size standard (manufactured by the company ABI), and 3.0 μl of unmodified amplified DNA product. A total volume of the sample for SSCP analysis was adjusted to 40 μl. The sample for SSCP analysis thus prepared was subjected to electrophoresis by applying a start-up voltage of 20 kV for 5 seconds up and then applying a voltage of 15 kV for 70 minutes. The electrophoretic results of 10 types (A to J) each gave two peaks (corresponding to two different allelic genes) in the test region for a gene. Based on measurement of the two peaks, a ratio of a target nucleic acid of interest to the nucleic acid of the other allelic gene was obtained and listed in Table 12.

[Table 12]

TABLE 12

The ratio of peaks in the test region of a gene

| | A | B | C | D | E | F | G | H | I | J |
|---|---|---|---|---|---|---|---|---|---|---|
| The ratio of peaks of nucleic acid derived from blood | 49 | 48 | 51 | 52 | 47 | 53 | 50 | 49 | 50 | 48 |
| The ratio of peaks of nucleic acid derived from tissue | 25 | 21 | 30 | 20 | 22 | 28 | 24 | 45 | 36 | 47 |
| The ratio of peaks of nucleic acid derived from urine | 34 | 43 | 32 | 51 | 45 | 42 | 33 | 40 | 31 | 30 |

5. Reexamination of Confidence Interval Based on the Ratio of Peaks and Determination of LOB Based on the results of Table 12 and Formulas (2) and (6), the threshold for determination of each of the test regions of genes, and the upper limit value and lower limit value thereof, from which the ratio of peaks of nucleic acid derived from tissue and urine were estimated, determination was made in consideration of such an upper limit and lower limit. To explain more specifically, if the upper limit of the ratio is lower than the threshold for determination, the test region of a gene was determined positive. In contrast, the lower limit of the ratio is higher than the threshold, the test region of a gene was determined negative. Furthermore, the threshold is interposed between the upper and lower limits, the determination cannot be made. The determination results are shown in Table 13.

[Table 13]

TABLE 13

Result of determination made on the basis of recheck of confidence interval and threshold for determination

| | A | B | C | D | E | F | G | H | I | J |
|---|---|---|---|---|---|---|---|---|---|---|
| Threshold for determination | 38 | 40 | 40 | 35 | 39 | 35 | 43 | 38 | 45 | 40 |
| Upper limit of the peak-ratio in tissue sample | 27 | 23 | 32 | 22 | 24 | 30 | 26 | 47 | 38 | 49 |
| Lower limit of the peak-ratio in tissue sample | 23 | 19 | 28 | 18 | 20 | 26 | 22 | 43 | 34 | 45 |
| Result of determination in tissue sample | + | + | + | + | + | + | + | − | + | − |
| Upper limit of the peak-ratio in urine sample | 41 | 57 | 46 | 66 | 59 | 56 | 47 | 54 | 44 | 43 |
| Lower limit of the peak-ratio in urine sample | 33 | 29 | 18 | 36 | 31 | 28 | 19 | 26 | 18 | 17 |
| Result of determination in urine sample | X | X | X | X | X | X | X | X | + | X |

Note:
+: positive,
−: negative,
X: impossible-to-determine

Re-examination was preformed by using Formulas (2), (3), (6), (7) based on the peak-ratio experimentally determined.

The results of the test were obtained statistically with a 95% degree of confidence. In this Example, the results were determined statistically with a 95% degree of confidence; however, more preferably, it can be made with a 99% degree of confidence.

Example 3

Detection of Viral Nucleic Acid in Blood

1. Determination of Conditions for Measurement

Viral nucleic acid contained in a small amount in blood can be detected by extracting nucleic acid (initial nucleic acid) from blood of a patient and subjecting the initial nucleic acid to amplification using a primer specific to a gene sequence of a virus. In this example, when the initial nucleic acid was sampled and added to an amplification reaction solution, it is possible to sample viral nucleic acid present in a concentration of not less than 0.01% in the initial nucleic acid with a 99% degree of confidence. The determination method will be explained below. To detect viral nucleic acid contained in a concentration of not less than 0.01%, p=0.0001 and statistic amount T=2.58 at a 99% degree of confidence were given. Determination of number of copies of initial target nucleic acid and determination of number of copies of nucleic acid in amplification reaction solution The nucleic acid extracted from human blood of a patient by the phenol/chloroform extraction method was used as the initial target nucleic acid. The concentration of the initial target nucleic acid was measured by a UV absorption apparatus. Assuming that the length of genomic DNA per cell is $4.0 \times 10^6$ kbp, the number of copies was calculated. The calculation results (the number of copies) are shown in Table 14. However, since the number of viral nucleic acid is unknown, it is determined by the number of copies of viral genome nucleic acid.

[Table 14]

TABLE 14

Concentration of initial target nucleic acid and the number of copies of initial nucleic acid

| Patient | DNA concentration (μg/μl) | Number of copies/μl | Total number of copies |
|---|---|---|---|
| Patient A | 5.0 | $1.05 \times 10^6$ | $5.25 \times 10^7$ |
| Patient B | 0.05 | $1.05 \times 10^4$ | $4.1 \times 10^4$ |

At this time, based on the recognition that a parent population is sufficient large since genomic nucleic acid derived from blood has not less than 100,000 copies, the number of copies of target nucleic acid in an amplification reaction solution was calculated in accordance with Formula (11). As is described above, the amount of nucleic acid required for amplification reaction or the number of copies were given and shown in Table 15.

[Table 15]

TABLE 15

The amount of target nucleic acid required for amplification and the number of copies thereof

| | The amount of nucleic acid | Number of copies |
|---|---|---|
| The amount of target nucleic acid to be sampled | 0.31 μg | $6.65 \times 10^4$ |

As a result, with respect to Patient A, the initial nucleic acid was partially diluted, sampled and subjected to determination. However, in the case of Patient B where the total number of copies of genomic nucleic acid was low and thus insufficient for analysis, trustworthy examination results might not be obtained. In this case, the genomic nucleic acid might not be used in analysis or analysis might be performed and thereafter a warning note or sign was attached in order to draw attention to the reliability of the final determination results.

What is claimed is:

1. A method of detecting or analyzing nucleic acid by simultaneously amplifying not less than two types of target nucleic acid samples having base sequences different in at least one base by using not less than two types of primers specific to sites of base sequences different in at least one base or not less than two types of primers specific to mutually different base sequences and analyzing a proportion of an amplified amount of nucleic acid of a target gene site in a target nucleic acid; the method comprising steps of:

amplifying nucleic acid by use of an amplification reaction solution containing the target nucleic acid;

estimating the number of copies of the target nucleic acid contained in the amplification reaction solution and the number of copies of initial target nucleic acid based on the amplified amount of nucleic acid after amplification or during amplification;

determining the number of copies of the target nucleic acid required in the amplification reaction solution by use of the number of copies of the initial target nucleic acid on the assumption that the probability that the number of the target nucleic acid copies in an aliquot is more than the necessary number of the target nucleic acid copies which is necessary for reliable test results obeys binomial distribution or normal distribution, when the aliquot is taken from the original sample solution which includes at least two types of target nucleic acid copies; and comparing the determined requisite number of copies with the estimated number of copies of the target nucleic: acid in the amplification reaction solution.

2. The method of detecting or analyzing nucleic acid according to claim 1, wherein a single strand conformation polymorphism analysis method is performed for detecting or analyzing nucleic acid by quantifying amplification amounts of two different nucleic acids.

3. The method of detecting or analyzing nucleic acid according to claim 1, wherein a dichromatic fluorescent nucleic acid microarray method is performed for labeling not less than two types of target nucleic acids with two different fluorescent dyes, respectively, amplifying the labeled target nucleic acids, measuring the fluorescent amounts of the amplified target nucleic acids by a fluorescent analysis method and analyzing the difference between the fluorescent amounts of the amplified target nucleic acids.

4. The method of detecting or analyzing nucleic acid according to claim 1, further comprising:

analyzing the proportion of amplified nucleic acid amount of a target gene site in the target nucleic acid, comparing the proportion of a target nucleic acid analyzed as a standard sample with the proportion of the target nucleic acid analyzed as a test sample, calculating the variations of the proportions of the not less than two types of target nucleic acids, and comparing the variations of the proportions of the not less than two types of target nucleic acids with a predetermined threshold, wherein if the variations of the proportions of the not less than two types of target nucleic acids is smaller than a predetermined threshold, it is determined that the proportion of not less than two types of target nucleic acids has not changed and if the variations of the proportions of the not less than two types of target nucleic acids is larger than or equal to a predetermined threshold, it is determined that the proportion of not less than two types of target nucleic acids has changed.

5. The method of detecting or analyzing nucleic acid according to claim 4, further comprising a step of amplifying target nucleic acid having the smallest proportion, of not less than two types of target nucleic acids having base sequences different in at least one base, by using not less than two types of primers specific to sites of base sequences different in at least one base or by using not less than two types of primer specific to sites of mutually different base sequences.

6. The method of detecting or analyzing nucleic acid according to claim 1, further comprising:
   calculating a confidence interval of the proportion of the target nucleic acid on the assumption that the probability that the number of the target nucleic acid copies in the aliquot is more than the necessary number of the target nucleic acid copies obeys binomial distribution or normal distribution, when an aliquot is taken from the original sample solution which includes at least two types of target nucleic acid copies.

7. The method of detecting or analyzing nucleic acid according to claim 1, further comprising a step of determining the number of copies of target nucleic acid in an amplification reaction solution by use of the number of copies of initial target nucleic acid on the assumption that the probability that the number of the target nucleic acid copies in the aliquot is more than the necessary number of the target nucleic acid copies obeys the Poisson distribution, when an aliquot is taken from the original sample solution which includes at least two types of target nucleic acid copies, the number of target nucleic acid copies being a few or several.

8. The method of detecting or analyzing nucleic acid according to claim 1, further comprising steps of
   preparing an amplification or analysis reaction solution by diluting or concentrating the initial target nucleic acid sample such that the number of copies of the target nucleic acid in the amplification or analysis reaction solution comes to be a predetermined value or more; and
   determining such an initial target nucleic acid sample that the number of copies of the target nucleic acid in the amplification or analysis reaction solution cannot be adjusted to the predetermined value or more; and
   when such initial target nucleic acid sample is not to be used for analysis, or analysis results are not be used as data if the initial target nucleic acid sample is used for analysis, or a description or a sign for warning is attached to the results of analysis using the initial target nucleic acid sample.

\* \* \* \* \*

UNITED STATES PATENT AND TRADEMARK OFFICE
CERTIFICATE OF CORRECTION

PATENT NO. : 7,585,628 B2  Page 1 of 1
APPLICATION NO. : 11/227233
DATED : September 8, 2009
INVENTOR(S) : Maeda et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 513 days.

Signed and Sealed this

Fourteenth Day of September, 2010

David J. Kappos
*Director of the United States Patent and Trademark Office*